United States Patent [19]

Antoku et al.

[11] Patent Number: 5,434,142
[45] Date of Patent: Jul. 18, 1995

[54] METHOD OF TREATMENT FOR MUSCULAR DYSTROPHY

[75] Inventors: Yasunobu Antoku; Kosuke Tsukamoto, both of Kurume; Fumihiko Koike, Saga; Tetsuo Sakai, Yame; Kaoru Tanaka, Fukuoka, all of Japan

[73] Assignee: MinoPhagen Pharmaceutical Company, Tokyo, Japan

[21] Appl. No.: 111,119

[22] Filed: Aug. 24, 1993

[30] Foreign Application Priority Data

Dec. 4, 1992 [JP] Japan .................. 4-325797

[51] Int. Cl.6 ........................... A61K 31/715
[52] U.S. Cl. .................... 514/53; 514/907
[58] Field of Search .................. 514/53, 907

[56] References Cited

FOREIGN PATENT DOCUMENTS

WOA9004399 5/1990 WIPO .

OTHER PUBLICATIONS

Dialog Information Services; File 155:Medline 1966–94; Accession No. 08087022; Abstract; and Eur. Neurol.; vol. 32, No. 1, 1992, pp. 44–51; S. Shintani et al; "Glycyrrhizin (licorice)-induced hypokalemic myopathy".
Bertorini, Tulio et al.; Muscle & Nerve; Jun. 1991; pp. 503–507; "Effect of Dantrolene in Duchenne Muscular Dystrophy".
Mendell, J. R., et al.; The New England Journal of Medicine; vol. 320, No. 24; Jun. 15, 1989; pp. 1592–1597; "Randomized, Double-Blind Six-Month Trial of Prednisone in Duchenne's Muscular Dystrophy".
Lewis and Elvin-Lewis *Medical Botany Plants Affecting Man's Health,* John Wiley and Sons Publisher (N.Y.), pp. 215, 275, 1977.
*Merck Manual,* pp. 1392–1393, 1982.

*Primary Examiner*—Raymond Henley, III
*Attorney, Agent, or Firm*—Knobbe, Martens, Olson & Bear

[57] ABSTRACT

Administering to a patient of muscular dystrophy a pharmaceutical agent containing glycyrrhizin and/or a pharmaceutically acceptable salt thereof as effective components is effective against muscular dystrophy, particularly, Duchenne or Becker muscular dystrophy and is highly safe with less side effect.

14 Claims, No Drawings

METHOD OF TREATMENT FOR MUSCULAR DYSTROPHY

BACKGROUND OF THE INVENTION

This invention relates to a method of treatment for muscular dystrophy and, more particularly, to a method of treatment for muscular dystrophy such as Duchenne muscular dystrophy, Becker muscular dystrophy and the like.

The Duchenne muscular dystrophy is a sex-linked recessive disease occuring in childhood, in which muscle weakness and muscular wasting in the proximal parts of extremities and trunk are progressed, resulting in a death at about twenty. The Becker muscular dystrophy is also a sex-linked recessive disease showing the same symptoms, although its onset age is older and tile progression is slower, compared with the Duchenne type.

Other muscular dystrophies include limb-girdle muscular dystrophy, facioscapulohumeral (FSH) muscular dystrophy, congenital muscular dystrophy, and the like.

Studies on these muscular dystrophies were widely made through many years in developed countries as leaders, with respect to the etiological cause, mechanism of incidence, medical treatment and the like, but, an effective medical treatment so far has not been established yet. Thus the earliest possible development of an effective remedy has long been awaited. Up to the present time, number of medicines were examined for their possibilities as the remedy, but prednisolone, a known 11-betahydroxy corticosteroid, and dantrolene are merely reported to be slightly effective.

Glyeyrrhizin has been used as a remedy for liver diseases and an anti-allergic medicine for many years, and its effectiveness is recognized. Although it causes hypokalemia as a side effect, this is relatively easy to control by the combined use with spironolactone. Further, glycyrrhizin is known to enhance the effects of adrenal cortical hormones by the suppression of metabolism of them, and it is also expected to reduce the side effect of prednisolone by the combined use with prednisolone.

However, glycyrrhizin has not been examined as a remedy for muscular dystrophy, and there has been no report on its effectiveness yet.

With respect to the prednisolone and dantrolene as the remedy for muscular dystrophy, it is the present state that troublesome adverse effects by their long-term use such as the production of a difficult side effect such as Cushing syndrome at a high ratio in case of the prednisolone and the induction of a liver damage in case of the dantrolene can not be avoided. The single use of these medicines can not provide a sufficient effect, and a new drug is desired which is well tolerated to the patients with muscular dystrophies for a long period, and can be used as an adjunctive therofy to prednisolone or dantrolene.

SUMMARY OF THE INVENTION

The present invention has a purpose to provide an effective and safe medical treatment for muscular dystrophy with less side effect.

As a result of the earnest studies to solve the above problems, the present inventors have found that glycyrrhizin known to be highly safe is effective for muscular dystrophy.

The present invention provides a method of treatment for muscular dystrophy which comprises the step of administering a pharmaceutical agent containing glycyrrhizin and/or pharmaceutically acceptable salts thereof as effective components to a patient. The method according to the present invention is particularly effective for Duchenne and Becker muscular dystrophies.

The present invention is further illustrated in detail.

The pharmaceutical agent used in the method of treatment according to the present invention contain glycyrrhizin and/or pharmacologically allowable salts thereof. Glycyrrhizin can be obtained by the extraction from licorice root. Commercially available ones may be also used. The pharmaceutically acceptable salts of glycyrrhizin include glycyrrhizin ammonium salt, glycyrrhizin alkali metal salts, glycyrrhizin choline salt and the like. These salts are obtained by reacting glycyrrhizin with inorganic or organic bases in molar ratio.

The drug form of the parmaceutically agent is not particularly limited, but, in general, they may be used in the form of injections and internal medicines such as powders, tablets, granules, capsules, solutions and the like. These can be manufactured by the use of conventionally known techniques.

Further, one or several kinds of pharmaceutically acceptable nontoxic fillers, for example, lactose, potato starch, calcium carbonate, and sodium alginate and the like may be added to these drugs. In the injection form, distilled water for injection, polyethylene glycol and the like may be used as a solvent, and a dispersing agent may be added thereto.

The method of treatment according to the present invention comprises the step of administering the pharmaceutical agent mentioned above to a patient of muscular dystrophy. As the administering method, either of oral and parenteral methods may be selected. The dose depends on the age and symptom of the patient, and in general, the dose in oral administration preferably ranges in an adult from 25-500 mg a day as the quantity of glycyrrhizin or its salt and, more preferably, a sufficient effect can be expected by the use within the range of 150-225 mg. The dose in paranteral administration is properly 40-400 mg a day in an adult.

The medical treatment for muscular dystrophy according to the present invention is effective for muscular dystrophies such as Duchenne type and Becker type muscular dystrophies, and safe with less side effect. It is expected to be effectively usable even in the combination with prednisolone and dantrolene, well-known cortisteroids.

DESCRIPTION OF PREFERRED EMBODIMENTS

Described below are preferred embodiments of the present invention. Examples of formulations used in the treatment for muscular dystrophy of the present invention are first illustrated.

Formulation Example 1 <Tablet>

A mixture of the following compositions is formed into a tablet in the usual way.

| | |
|---|---|
| Glycyrrhizin | 25 mg |
| Potato starch | 270 mg |
| Magnesium stearate | 5 mg |

| | |
|---|---|
| Total | 300 mg |

Formulation Example 2 <Sugar-coated tablet>

A mixture of the following compositions is formed into a sugar-coated tablet in the usual way.

| | |
|---|---|
| Glycyrrhizin | 25 mg |
| Aminoacetic acid | 25 mg |
| Methionine | 25 mg |
| Precipitated calcium carbonate | Proper quantity |
| Lactose | Proper quantity |
| Carboxymethylcellulose | Proper quantity |
| Total | 300 mg |

Formulation Example 3 <Granule>

A mixture of the following compositions is formed into a granule in the usual way.

| | |
|---|---|
| Glycyrrhizin | 25 mg |
| Lactose | 210 mg |
| Starch | 60 mg |
| Gelatin | 5 mg |
| Total | 300 mg |

Formulation Example 4 <Injection>

To an isotonic sodium chloride solution, 200 mg of glycyrrhizin is dissolved into 100 ml, and formed into an injection in the usual way.

Formulation Example 5 <Injection>

To an isotonic sodium chloride solution, 200 mg of glycyrrhizin, 2000 mg of aminoacetic acid, and 100 mg of cysteine are dissolved into 100 ml, and formed into an injection in the usual way.

Pharmacological Test

The effect of the treatment for muscular dystrophy of the present invention is illustrated in reference to a clinical test.

1. Subject

Subjects were 17 patients of Duchenne muscular dystrophy (age 13–22, average age 17.6) and 4,patients of Becker muscular dystrophy (age 15–64, average age 44.5). The subjects was diagnosed by five doctors approved by the Japanese Society of Neurology on the basis of the present history, clinical symptoms, neurological examinations, neurophysiological tests and muscle biopsy.

2. Used agents

As a muscular dystrophic remedy containing glycyrrhizin and/or its pharmaceutically acceptable salt, Glycyrrhon as internal tablets and Stronger Neo-Minophagen C as an intravenous injection (the both are made by MINOPHAGEN PHARMACEUTICAL CO., Trademarks) were employed. The prescriptions of Glycyrrhon and Stronger Neo-Minophagen C are as follows.

<Glycyrrhon tablet>

A white sugar-coated tablet containing the following components in one tablet.

| | |
|---|---|
| Glycyrrhizin | 25 mg |
| DL-Methionine | 25 mg |
| Aminoacetic acid | 25 mg |
| Precipitated calcium carbonate | 25 mg |

<Stronger Neo-Minophagen C>

The following components are contained in one ample (20 ml).

| | |
|---|---|
| Glycyrrhizin ammonium | 40 mg (as glycyrrhizin) |
| Aminoacetic acid | 400 mg |
| L-cysteine hydrochloride | 20 mg |

As additives, 16 mg of sodium sulfite and proper amount of 10% of ammonia water are added.

3. Method for the test

Administration dose hereinbelow shows quantity of glycyrrhizin.

The 17 patients of Duchenne type muscular dystrophy were divided into 12 of medication group and 5 of nomedication group at random. All the patients of the medication group were subjected to continued administration of tablets (150 mg/day), or continued administration of tablet (150 mg/day) after intravenous injection (40 mg/day) for 2 weeks, and the results were observed.

On the other hand, the patients with Becker muscular dystrophy were subjected to continued administration of tablets (225 mg/day), or continued administration of tablets (225 mg/day) after intravenous injection (80 mg/day) for 4 weeks, and the results were observed. Informed consents were obtained from all the medicated patients and their families.

The evaluation was carried out with respect to muscule strength and function by using the criteria by Brooke et al. (Brooke, M. H. et al., Muscle Nerve 4, 186–197, 1981). The 18 muscle groups shown in Table 1 were evaluated for muscle strength according to the criteria shown in Table 2 before starting the administration and 4, 8 and 12 weeks after administration, and respective mean muscle strength scores were calculated. As an index evaluating extremity functions, a 3×3 inch square clipping test was conducted, and the required time therefor was taken as the index. The reason for using this test for the evaluation of extremity functions is that the abilities for locomotion of the subject patients were low, and this is the only test that all the patients can undergo for evaluating the extremity functions.

The mean muscle strength score and the change ratio of the required time in the 3×3 inch square clipping test were compared between the medication group and the no-medication group. The assessment was performed by the five doctors approved by the Japanese Society of Neurology.

Further, routine laboratory tests such as peripheral blood picture, liver function test, and urinalysis were similarly carried out.

TABLE 1

| Evaluated Muscle Groups | |
|---|---|
| Muscle Groups | Muscle Groups |
| shoulder abduction | hip abduction |
| shoulder external rotation | knee flexion |
| elbow flexion | knee extention |
| elbow extention | ankle inversion |
| wrist flexion | ankle eversion |
| wrist extention | ankle plantar flexion |
| thumb abduction | ankle dorsiflexion |

TABLE 1-continued

| Evaluated Muscle Groups | |
|---|---|
| Muscle Groups | Muscle Groups |
| hip flexion | neck flexion |
| hip extention | neck extention |

TABLE 2

| Grade | Degree of Strength | Score |
|---|---|---|
| 5 | Normal muscular strength | 10 |
| 5− | Slightly hypothenic | 9 |
| 4s | Middle between 5− and 4 | 7 |
| 4 | Hyposthenic, but movable against combination of gravity and resistance | 7 |
| 4w | Middle between 4 and 3+ | 7 |
| 3+ | Temporarily movable against resistance, but becomes unmovable soon | 5 |
| 3 | Unmovable to addition of resistance, but movable against gravity | 4 |
| 3− | Movable against gravity, but the movable range is not perfect | 3 |
| 2 | Movable in the state having no gravity | 2 |
| 1 | Slightly movable | 1 |
| 0 | Entirely unmovable | 0 |

The results are shown in Tables 3 and 4. A significant difference was recognized between the no-medication group and the medication group with a P value less than 5% (P<0.05). For the test, the Wilcoxon's two-sample rank test (Wilcoxon, F. Individual comparison by ranking methods. Biometrics, 1, 80–83, (1945); Wilcoxon, F. Probability tables for individual companions by ranking methods. Biometrics, 3, 119–122, (1947)) was adapted.

TABLE 3

| Change Ratio of Mean Muscle Strength | | | | | |
|---|---|---|---|---|---|
| Duchenne type medication group (%) | | Becker type medication group (%) | | Duchenne type no-medication group (%) | |
| Before medication | 0 0 0 | 0 0 | 0 0 | 0 | 0 0 | 0 |
| 4th week | 0 8.9 | 38.2* | 0 0.6 | 2.2* | −8.0 −4.3 | −2.0 |
| 8th week | 0 17.7 | 62.2* | 0 0.9 | 2.1* | −12.2 −8.4 | −4.5 |
| 12th week | 0 19.7 | 62.2* | 0 3.6 | 6.2* | −18.7 −11.2 | −5.7 |

Upper numbers show range, and lower numbers show mean.
Minus change ratio means deterioration, and plus change ratio means improvement.
*: significantly different with P value less than 5%, compared with no-medication group.

TABLE 4

| Change Ratio of Required Time in 3 × 3" Square Clipping Test | | | | | |
|---|---|---|---|---|---|
| Duchenne medication group (%) | | Becker medication group (%) | | Duchenne no-medication group (%) | |
| Before medication | 0 0 | 0 | 0 0 | 0 | 0 0 | 0 |
| 4th week | 7.1 −20.6 | −42.6* | −9.5 −31.4 | −44.4* | 34.6 9.4 | −12.2 |
| 8th week | 1.8 −22.2 | −40.0# | −27.3 −38.3 | −47.2* | 12.7 −7.7 | −20.5 |
| 12th week | 7.1 −28.0 | −49.3* | −36.1 −46.1 | −57.8* | 23.6 −1.4 | −14.4 |

Upper numbers show range, and lower numbers show mean.
Minus change ratio means improvement, and plus change ratio means deterioration.
*: significantly different with a risk less than 5%, compared with no-medication group.
: not significant different with a risk of 5–10% compared with no-medication group.

The results shows that the treatment according to the present invention has therapeutic effects to the reduction in muscular strength and/or reduction in extremity function of the Duchenne and Becker muscular dystrophies.

Since this effect is supposed to be due to the action of stabilizing cell membranes and action of suppressing calcium separation from sarcoplasmic reticula possessed by the glycyrrhizin which is the effective component of the remedy used in the treatment of the present invention, the similar effect to other muscular dystrophies of the same morbid state can be expected. Hypokalemia emerged in two of twelve patients in Duchenne muscular dystrophy and in two of four patients in Becker muscular dystrophy, but it was improved by the combined use with 25 mg–50 mg/week of spironolactone. No side effect emerged in the others. Acute Toxicity Test for Glycyrrhizin Glycyrrhizin shows the following $LD_{50}$, and is low toxic.

| (1) Oral administration (rat) | 3 g/kg< |
|---|---|
| (2) Subcutaneous injection - 5% aq. soln. (mouse) | 1873.3 mg/kg |
| (3) Intravenous injection - 2% aq. soln. (mouse) | 682.5 mg/kg |
| (4) Intraperitoneal injection - 0.2% aq. soln. (mouse) | 225–244 mg/kg |

What is claimed is:

1. A method of treatment for muscular dystrophy consisting essentially of the step of administering to a patient having muscular dystrophy a pharmaceutical agent consisting essentially of glycyrrhizin in an amount effective to treat muscular dystrophy, wherein said composition excludes ingredients other than glycyrrhizin that would materially affect the basic characteristics thereof.

2. A method according to claim 1 wherein the glycyrrhizin has the form of a pharmaceutically acceptable salt.

3. A method according to claim 2 wherein the salt is selected from the group consisting of ammonium salt, alkali metal salts, choline salts, and mixtures thereof.

4. A method according to claim 1 wherein the pharmaceutical agent has the form selected from the group consisting of powders, tablets, granules, capsules, solutions and injections.

5. A method according to claim 1 wherein the pharmaceutical agent is orally administered, and the per capita daily dose is 25–500 mg as the quantity of glycyrrhizin.

6. A method according to claim 1 wherein the pharmaceutical agent is paranterally administered, and the per capita daily dose is 40–400 mg as the quantity of glycyrrhizin or its salt.

7. A method according to claim 1, wherein the muscular dystrophy is of Duchenne or Becker.

8. A method of treatment for muscular dystrophy comprising the step of administering to a patient having muscular dystrophy a pharmaceutical agent containing glycyrrhizin in an amount effective to treat muscular dystrophy, provided that glycyrrhizin is not administered in conjunction with a corticosteroid.

9. A method according to claim 8, wherein the glycyrrhizin has the form of a pharmaceutically acceptable.

10. A method according to claim 9, wherein the salt is selected from the group consisting of ammonium salt, alkali metal salts, choline salts, and mixture thereof.

11. A method according to claim 8, wherein the pharmaceutical agent has the form selected from the group consisting of powders, tablets, granules, capsules, solutions and injections.

12. A method according to claim 8, wherein the pharmaceutical agent is orally administered, and the per capita daily dose is 25–500 mg as the quantity of glycyrrhizin.

13. A method according to claim 8, wherein the pharmaceutical agent is parenterally administered, and the per capita daily dose is 40–400 mg as the quantity of glycyrrhizin or its salt.

14. A method according to claim 8, wherein the muscular dystrophy is of Duchenne or Becker.

* * * * *